United States Patent [19]

Manns et al.

[11] Patent Number: 5,705,749
[45] Date of Patent: Jan. 6, 1998

[54] USE OF ULTRASONOGRAPHY TO EVALUATE SIZE AND ECHOTEXTURE OF GONADAL AND ACCESSORY GENITAL STRUCTURES IN DOMESTIC ANIMALS

[75] Inventors: John G. Manns; Gregg P. Adams; Roger A. Pierson, all of Saskatoon, Canada

[73] Assignee: Biostar Inc., Saskatchewan, Canada

[21] Appl. No.: 533,503

[22] Filed: Sep. 25, 1995

[51] Int. Cl.$^6$ .............................. A61B 8/00; G01N 29/06
[52] U.S. Cl. .................. 73/602; 73/634; 128/660.01; 128/660.07
[58] Field of Search ...................... 73/597, 599, 602, 73/620, 627, 629, 634, 628; 128/660.01, 660.07, 633, 661.03

[56] References Cited

U.S. PATENT DOCUMENTS

| | | | |
|---|---|---|---|
| 4,073,289 | 2/1978 | Fahim | 128/842 |
| 4,384,206 | 5/1983 | Bjarno | 250/339.12 |
| 4,563,428 | 1/1986 | Mortensen | 436/21 |
| 4,610,877 | 9/1986 | Brooks et al. | 424/195.11 |
| 4,785,817 | 11/1988 | Stouffer | 128/660.07 |
| 4,906,563 | 3/1990 | Singh et al. | 435/7.92 |
| 5,079,951 | 1/1992 | Raymond et al. | 73/602 |
| 5,339,815 | 8/1994 | Lin et al. | 128/660.01 |
| 5,344,780 | 9/1994 | Nonboe | 436/21 |
| 5,348,002 | 9/1994 | Caro | 128/633 |
| 5,353,796 | 10/1994 | Schroeder et al. | 128/660.01 |
| 5,372,822 | 12/1994 | Fahim | 424/643 |
| 5,442,572 | 8/1995 | Kiridena et al. | 364/560 |
| 5,483,441 | 1/1996 | Scofield | 364/400 |
| 5,573,002 | 11/1996 | Pratt | 128/660.07 |

OTHER PUBLICATIONS

H.B. Oonk, J.A. Turkstra, H. Lankhof, W.M.M. Schaaper, J.J.M. Verheijen & R.H. Meloen: "Testis size after immunocastration as parameter for the absence of boar taint", Livestock Production Science 42 (1995) pp. 63–71.

R.H. Meloen, J.A. Turkstra, H. Lankhof, W.C. Puijik, W.M.M. Schaaper, G. Dijskstra, C.J.G. Wensing & R.B. Oonk, "Efficient immunocastration of male piglets by immunoneutralization of GnRH using a new GnRH–like peptide", Vaccine, 1994, vol. 12, No. 8, pp.741–746.

M. Bonneau, R. Dufour, C. Chouvet, C. Roulet, W. Meadus and E.J. Squires, "The Effects of Immunization Against Luteinizing Hormone–Releasing Hormone on Performance, Sexual Development, and Levels of Boar Taint–Related Compounds in Intact Male Pigs". J. Amin. Sci. 1994, 72; pp. 14–20.

*Primary Examiner*—Hezron E. Williams
*Assistant Examiner*—Rose M. Miller
*Attorney, Agent, or Firm*—Michael, Best & Friedrich

[57] ABSTRACT

Ultrasonography together with computer analysis tools are used to obtain measurements of gonadal density and size in male livestock, and particular in immunologically castrated boars in a slaughterhouse. These measurements are compared with reference thresholds with the main purpose of determining whether the immunologically castrated boars have entered puberty. Boars are likely to be subject to meat tainting subsequent to the onset of puberty due to biological secretions which occur at that time. This method allows the majority of tainted meat to be screened out prior to delivery.

12 Claims, 5 Drawing Sheets

USE OF ULTRASONOGRAPHY TO EVALUATE SIZE AND ECHOTEXTURE OF GONADAL AND ACCESSORY GENITAL STRUCTURES IN DOMESTIC ANIMALS

BACKGROUND OF THE INVENTION

The invention relates to immunological castration of male livestock, specifically a method appropriate for high-volume screening of immunologically castrated livestock to determine whether immunological castration was successful in preventing meat tainting.

Currently, in much of the world, male pigs are castrated shortly after birth because meat from pigs that are left intact until the time of slaughter will have an odour referred to as boar taint. Boar taint is comprised of two primary components. One compound is skatole derived from metabolism of tryptophan in the gastrointestinal tract. The second, and more important of the boar taint compounds, is androstenone which is a steroid produced by the Leydig cells of the testes. The production of this molecule is regulated by pituitary gonadotrophins and is produced as the pig begins to reach sexual maturity. Generally, pigs slaughtered at weights of up to 80–90 kg do not have significant boar taint because sexual maturity will not have been achieved. However, at the usual market weight of 105–125 kg, in North America, a significant proportion of boars will have tainted meat because some of these animals will have reached puberty.

There are important advantages to raising intact males compared to castrates. Boars are approximately 10% more efficient in feed conversion (Hansson, Swedish J. Agric Res. 4,209, 1974) and their carcasses have about 6% more muscle and 8% less fat (Knudson et al J. Anim. Sci,61:787, 1985). One way of-raising intact males, which is currently done in Great Britain, is to slaughter the animals below 90 kg which insures that the majority of pigs will have minimal risk of being tainted because they will not have begun to produce androstenone in significant quantities. However, in much of the world, pigs are raised to heavier weights because of economic advantages which relate to size of cuts and efficiencies which result from amortizing the cost of the larger carcasses against fixed costs such as facilities and breeding stock. For instance, meat slaughtering and processing facilities can achieve higher throughput with larger carcasses.

Currently, the procedure to avoid boar taint due to androstenone is to castrate pigs shortly after birth. However, techniques have been described involving an immunological approach to block gonadal endocrine function. Most of these techniques rely on the production of active immunity to Gonadotrophin Releasing hormone (GnRH), a 10 amino acid hypothalmic peptide first described in 1971 (Schally et el, Biochem Biophys Res. Commun., 43,393, 1971). Two recent papers (Bonneau et el, Anim Sci., 72,14, 1994, Meloen et el, Vaccine, 12,741, 1994) describe procedures where a priming injection of an antigen given early in the life of the animal (eg., at weaning) is followed by a booster injection given several weeks prior to the expected date of slaughter. The basis of this method is that the first injection primes the immune response but does not provide a biologically effective increase in antibody titres and consequently the development of the testes and endocrine function are not altered significantly. This means that the desired anabolic effects of testosterone are present for much of the growth period. The booster injection stimulates a strong antibody response, with antibody titres that neutralize the production of the pituitary gonadotrophins which regulate gonadal function. In the absence of gonadotrophin support, the testes will begin to regress and androstenone and testosterone production will fall dramatically. The timing of the second injection is intended to ensure that any androstenone present at the time of the second injection will have leached out of fat and muscle over the last 2–3 weeks of the animals' life.

However, such procedures may not be 100% efficacious and it is impossible to determine if meat is tainted, using simple powers of observation. There is no rapid, inexpensive test to determine accurately if tissues contain unacceptable levels of boar taint compounds. Methods have been developed to detect skatole and androstenone (Claus et al, Arch fur Lebensmittelhygiene, 39,85, 1988, Squires, Can. J. Anim. Sci., 70:1029, 1990); however, these procedures are moderately costly and not ideal to use in a high-volume slaughterhouse setting. Therefore, it would be desirable to have some method of detection which could screen out the vast majority of animals with minimal risk of boar taint. Then, animals at risk of having boar taint could either be utilized in a different fashion (eg. cooked or spiced meats), or the carcasses in question could be analysed for the specific boar taint compounds to determine which carcasses truly are tainted.

Most methods disclosed in the prior art for testing whether boar taint is present are chemical in nature, measurements being made of the degree to which lndole compounds associated with boar taint are present in samples taken from the animal. For example, in U.S. Pat. Nos. 5,344,780 and 4,563,428 the steps include obtaining a sample, heating the sample to melt fat in the sample, and extracting at least a portion of the sample with a polar solvent and then analysing the contents of the extracted sample through various means. The method of U.S. Pat. No. 4,906,563 includes the steps of combining a sample and anti-skatole antibodies in a reaction buffer, incubating for a time sufficient to form an antibody-skatole complex, and determining the amount of antibody-skatole complex as an indication of boar taint in the pig.

Other methods do not require chemical reactions, but still require complex statistical analysis. For example, U.S. Pat. No. 4,384,206 employs infrared spectrophotometry, using the difference in infrared absorption of a particular wavelength between boar tainted meat and meat without boar taint to determine, on a statistical basis, whether boar taint is present. Another method described in U.S. Pat. No. 5,233,780 measures the content of boar taint-producing indoles in a sample through UV detection or direct fluorometric determination.

A problem with these methods is that the required experiments or analyses are of substantial complexity and cost. In a high-volume slaughterhouse, the time taken by these methods for detection of boar taint may also be a problem.

In a recent publication Oonk et al (Livestock Prod Sci., 42,63–71, 1995) have described the relationship between testicular weight and length and androstenone concentrations in adipose tissue, and show that, within limitations, testes weight can be a useful screening method. One way of evaluating testicular size would be to remove the tissue on the slaughter line and to weigh it. However, in a high through-put plant this could be problematic and, such simple observation would not allow measurement of volume or tissue composition. No suggestion has been made of a method of quickly and cost-effectively utilizing the theoretical result of Oonk's paper in a commercially viable context.

3

SUMMARY OF THE INVENTION

It is an object of the present invention to provide an ultrasonographic method and means for determining the sexual maturity of a male animal.

It is another object of the invention to provide a method and means for measuring whether male animals have been successfully immunocastrated.

It is another object of the present invention to provide a method and means for determining the likelihood of boar taint in pigs which may have been immunologically castrated, the method being appropriate for a high-volume, high-speed slaughterhouse.

According to a first broad aspect, the invention provides a method of determining sexual maturity of an animal by subjecting a sexual organ of the carcass of the animal to ultrasonographic scanning. Measurement of the size or echotexture of the sexual organ will be compared with reference values to provide an indication of the sexual maturity of the animal.

According to a second broad aspect, the invention provides an apparatus for determining the sexual maturity of animal carcasses comprising means for conveying the carcasses, artificial vision means for locating a sexual organ of each of the carcasses as they are conveyed, an ultrasonic scanner having an ultrasonic transducer, means dependent on the artificial vision means for positioning the ultrasonic transducer in relation to the sexual organs to carry out ultrasonic scanning of the sexual organs, computing means connected to the ultrasonic scanner to compute from signals input from the ultrasonic scanner values for the volume or texture of the sexual organs and derive therefrom an indication of the sexual maturity of the carcasses.

The fundamental basis for the use of this non-invasive, real-time technique is that tissues vary in their ability to transmit or reflect sound waves. Electrical impulses from an ultrasound console are converted into ultrasound waves by a transducer which is placed in contact with the tissue of interest. The pattern or intensity of reflected sound waves (echo) are amenable to quantitative analysis.

For the purpose of directing the ultrasound transducer to the correct location on the animal, an artificial vision apparatus may be employed. This may include a video camera together with software, the software being able to calculate from recorded images the location of specific recognizable landmarks such as a hook on the line, or a leg of the animal being analysed. These locators would then be used to orient and guide the camera to the scrotal area, which in turn would be the visual guide used to orient the ultrasound transducer. As a final stage in determining whether the correct location has been achieved, the range of measurements produced by the ultrasound scanner would be compared with preset values. If measurements exceed pre-set extremes, improper locations will be assumed and further guiding using artificial vision will be attempted. Once accurate location is achieved, a decision is generated as to the most likely physiological status of the structure being scanned.

The present invention provides specific application of such technology in the evaluation of the size and texture of the testicles, epididymides, vesicular glands and bulbo urethral glands in boars.

The new way of evaluating the dimensions of a gland, such as the testes or the accessory sex glands, is to use ultrasonography as an analytical tool. Advantages of using ultrasonography include the fact that measurements can be made rapidly in tissues in situ, or after tissue removal. Using this technology one can measure the dimensions (ie., length, width, depth) and, using an appropriate algorithm, calculate volume. Based on the echotexture of the tissue, it is also possible to determine whether or not the texture is different from a standard which has been established previously. Since, it is well known to those experienced in the art, that the structure of gonadal tissues changes dramatically after animals are immunized against gonadotrophin releasing hormone, the texture of these tissues would be substantially different in immunized compared to control animals. This difference in tissue texture is reflected in the intensity of the reflected ultrasound waves. Some tissues and fluids conduct sound waves much better than others. Consequently, a tissue which conducts sound waves poorly has a strong echo. Over the period of time that the gonadal tissues develop, tissue composition changes resulting in a different ultrasound image echotexture. Major, or even subtle changes in the consistency of a tissue due to maturation or change in physiological function are detectable as an alteration in echotexture. The absolute density measurement itself may be used as an indication of the maturity of the animal. A number and degree of variation is generated as a measurement of echotexture based on an arbitrary but standardized scale.

Furthermore, based on echotexture measurements, it is possible to interpret abrupt changes in tissue density as boundaries between different types of tissue, or between a tissue and the background. An appropriate algorithm may then be used which calculates the dimensions, area or volume of the tissue being scanned.

The ultrasound measurements (dimensions and echotexture) will be converted, using computer programs, to specific values and compared to predetermined thresholds (eg., volume threshold of 150 $cm^2$ and an echo density threshold of 5 on a scale of 1 to 10). Anything less than these thresholds with either measurement independently would indicate that the pig is negative for taint. It is also conceivable that a value of 160 $cm^2$ and a density of 6 could trigger a similar negative response because experiments might indicate that two marginal but independent results would be correlated strongly with a negative result. These numbers are completely theoretical and given for illustration purposes only.

DESCRIPTION OF THE PREFERRED EMBODIMENT

Referring to FIGS. 1a–1d, representations are shown of histological sections of testes (1a, 1b) or prostate (1c, 1d) of control or GnRH immunized animals. The representations clearly show that significant differences in tissue texture occur in immunized compared to control animals.

The concept, as disclosed, describes the use of ultrasonography as a method to be applied routinely to evaluate gonadal or accessory genital structures in domestic animals. The concept, as described here, relates primarily to the use of ultrasonography as a method to identify boars that have normal gonadal size or texture compared to animals that have been subjected to immunological castration. However, it could also apply to non-immunized animals, particularly those slaughtered at lighter weights. The specific utility of this invention is, therefore, as a simple inexpensive method to identify animals which may have boar taint.

The method is also applicable to species such as beef cattle, where testicular size and texture can also be a method for evaluating the presence or absence of functional testicular tissue as a means of confirming whether animals have been successfully immunocastrated.

Figure 1A:
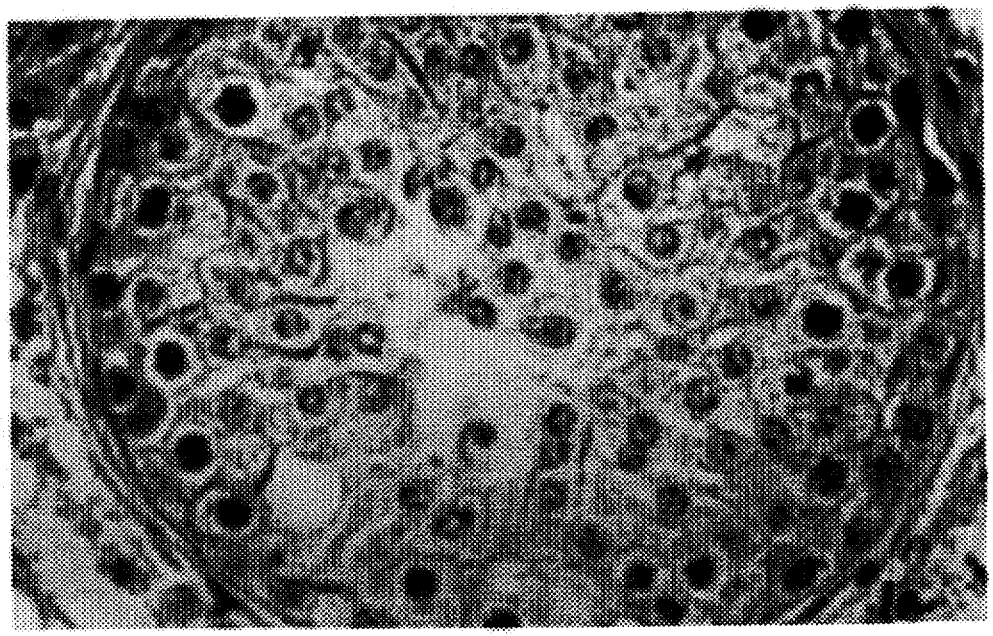
FIG. 1a is a micrograph of the testes of a control animal.
Figure 1B:
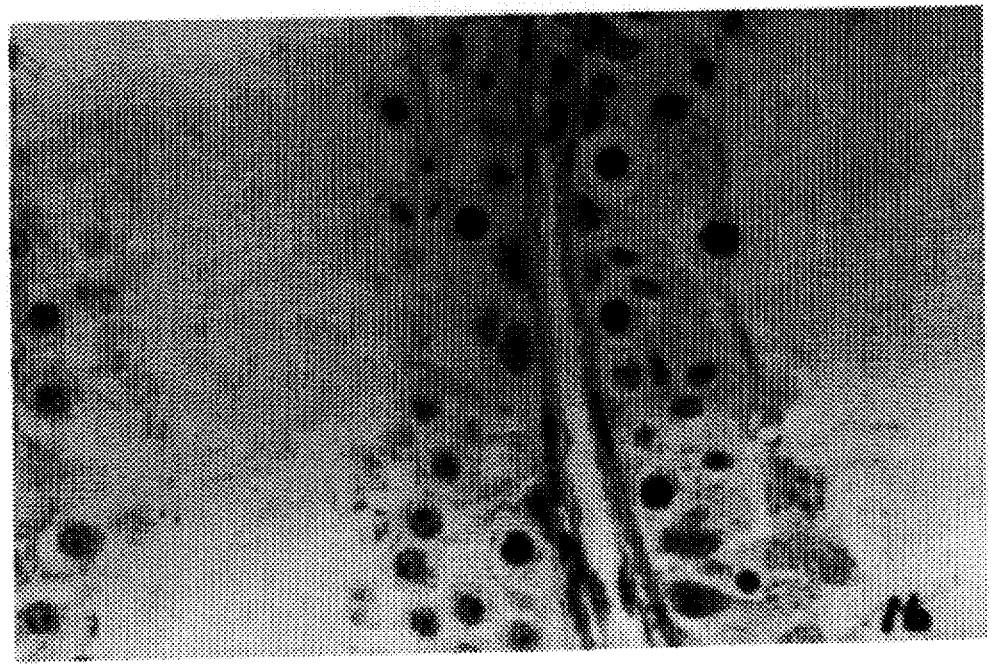
FIG. 1b is a micrograph of the testes of an immunized animal.
Figure 1C:
FIG. 1c is a micrograph of the prostate gland of a control dog.
Figure 1D:
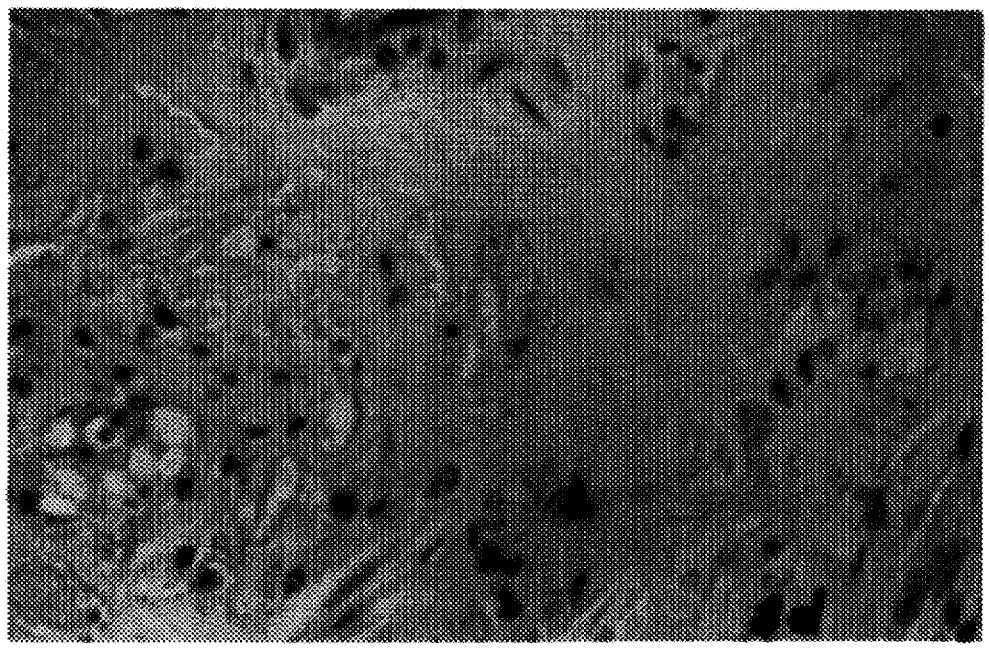
FIG. 1d is a micrograph of the prostate of an immunized dog.
Figure 2:
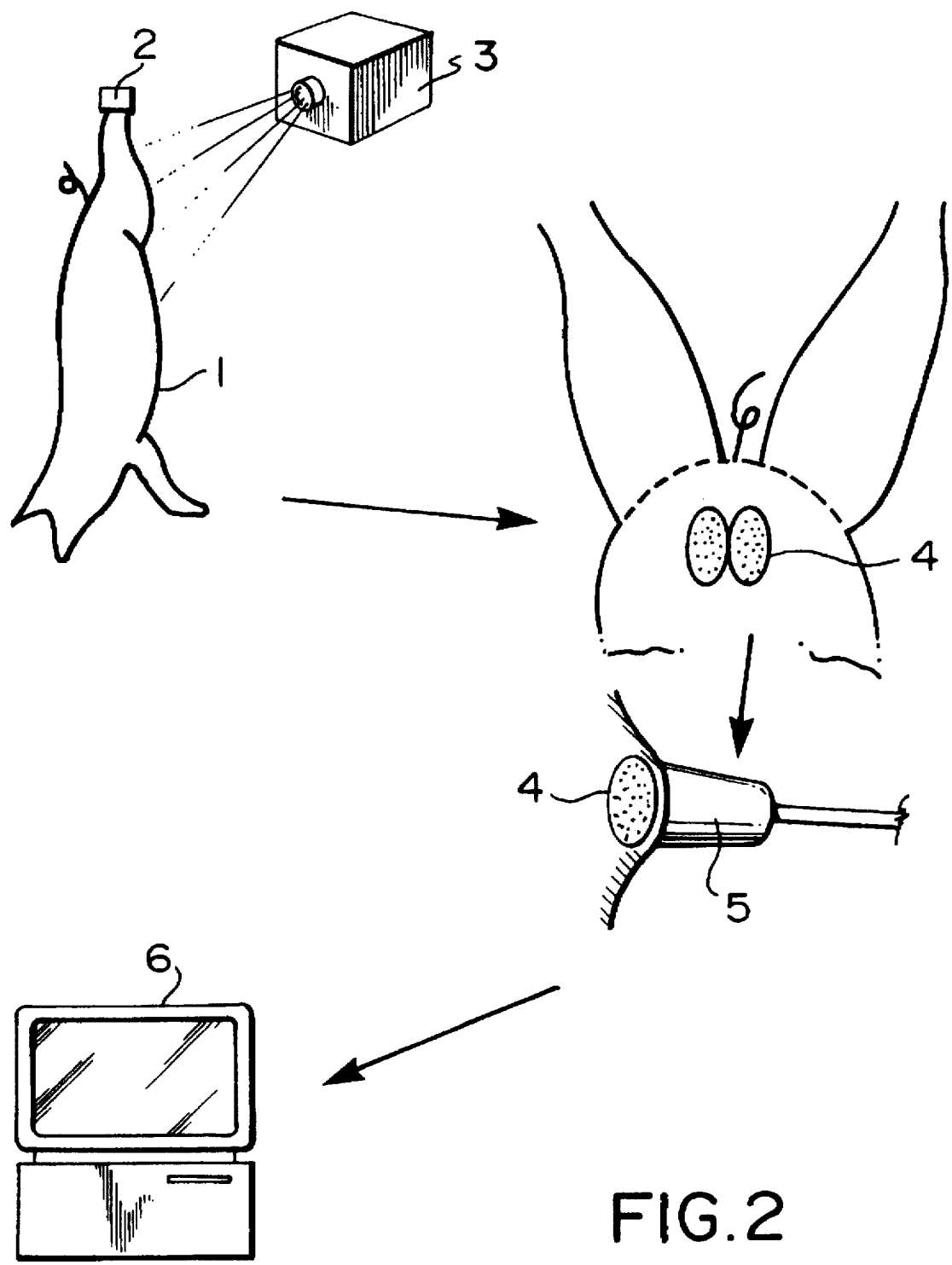
FIG. 2 is a pictorial representation of a method and apparatus for scanning testis of a pig at slaughter.

The method we describe can be used on tissues which have been removed from animals and fed into an automated device which allows the measurement and the recording of the parameters that are calculated or, it is possible to do the measurements on the intact animals as they proceed through the slaughter line. This concept is depicted in FIG. 2.

In this example, after the animals 1 are killed and hung on a line 2, a detection device consisting of a unit for artificial vision 3 locates the testes 4, and positions the ultrasound transducer 5 over one of the testes. A measurement of length, width, depth or other parameters is made as well as an estimation of the echotexture of the tissue. The dimensions are transmitted to a computer 6 programmed to contain an algorithm appropriate to the calculation of volume or other measurement closely correlated with testicular function as assessed by androstenone or testosterone production; echo texture is also analysed. If the combination of texture and structural dimensions falls within a range where animals were known, based on previous experiments, to have a very low likelihood of having boar taint, then the tissues from the animals are processed without any further need to assess tissue for the presence of boar taint compounds. On the other hand, if the parameters measured were above a certain trigger level, the carcass is identified and fat tissue from those carcasses is evaluated separately by chemical methods to determine if boar taint compounds are in fact present. Using such techniques, a high proportion of animals can be screened out without necessity for any chemical analysis.

This procedure allows for the use of a very rapid accurate screening procedure and is an important development to allow the raising of intact animals using an immunological castration procedure to prevent boar taint.

The typical time required using this technique to determine whether an animal has successfully been immunologically castrated is 5 seconds. This allows the process to be used in a high volume slaughter-house setting.

Figure 3A:
FIG. 3 shows ultrasound images of the test is of a bull calf at 5 weeks of age (left) and 35 weeks of age (right)
Figure 3B:

FIG. 3 shows ultrasound images of the testis of a bull calf at five weeks of age in the left photo, and at 35 weeks of age in the right photo. The arrows indicate the medial and lateral borders of a testis. The difference in pixel intensity of the testicular tissue is clearly evident in these photos.

Figure 4A:
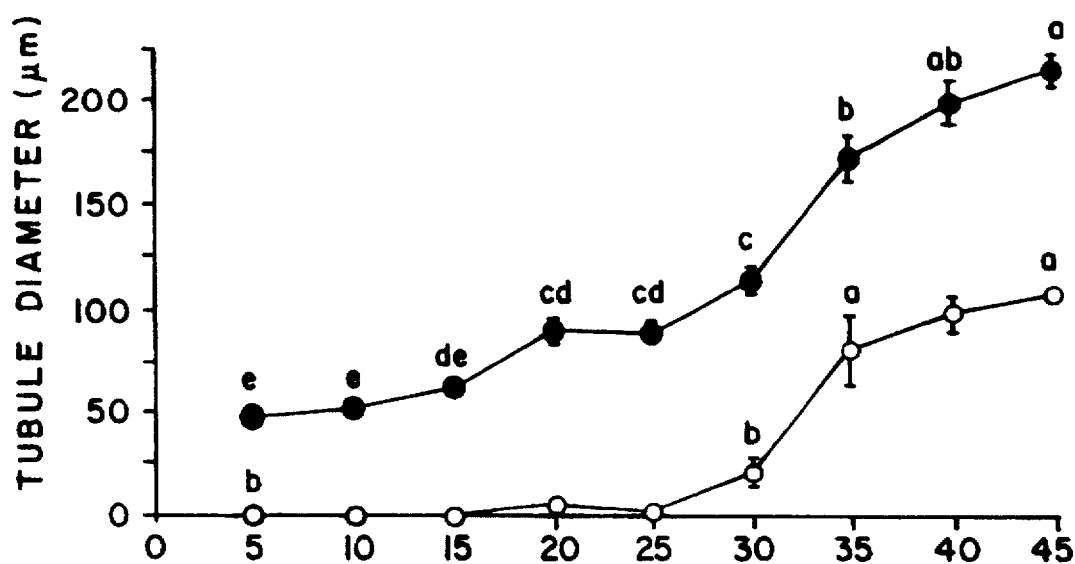
FIG. 4 shows the mean inner and outer seminiferous tubule diameters in testes collected from bull calves as a function of time in weeks (upper graph), and the mean pixel intensities from ultrasound images of testes of bull calves at 2-week intervals from 2 to 40 weeks of age (lower graph).
Figure 4B:
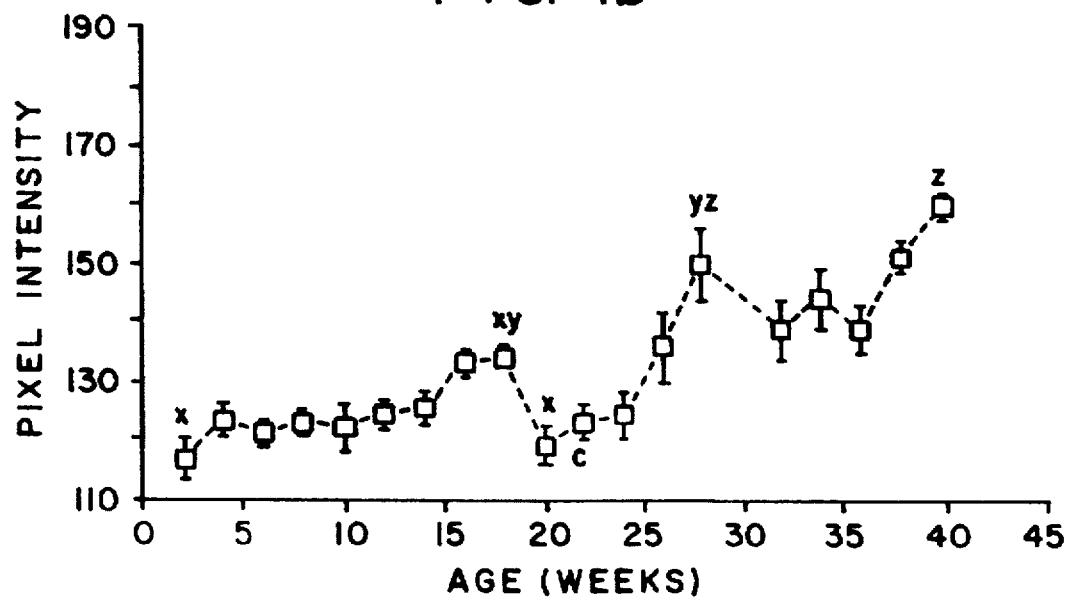

To evaluate the ultrasound as a method to determine both the dimensions and echo density of testicular tissue, 10 bull calves were evaluated at two week intervals from two to 40 weeks of age. Puberty in bulls typically begins at six to eight months and most animals would be sexually mature by 15 months of age. Ultrasound measurements were made with an Aloka SAD500 machine with a 7.5 or 5 MHZ linear-array transducer. Measurements of tubule diameter and testicular diameter (not shown) were made using integrated electronic calipers. The upper graph in FIG. 4 plots the mean inner and outer seminiferous tubule diameters in testes collected from bull calves as a function of age in weeks. The lower graph in FIG. 4 plots the mean pixel intensities from ultrasound images of testes of bull calves at two week intervals. The data demonstrate that it is practical to use the technique to measure dimensions and also confirms that it is possible to detect significant changes in echotexture (recorded as pixel intensity) as a function of change in the state of sexual maturity of animals.

What is claimed is:

1. A method of determining the state of gonadal function of an animal comprising subjecting a sexual organ of the carcass of the animal to ultrasonic scanning, obtaining from the ultrasonic scanning a measurement of the size or texture of the sexual organ, comparing the measurement with stored reference values and determining from the comparison an indication of the gonadal function of the animal.

2. The method of claim 1 wherein the animal whose state of gonadal function is to be determined is a boar, and comprising the further step of using the indicated state of gonadal function as an indication of the likelihood of boar taint.

3. The method of claim 1 wherein the animal is one which has been previously subjected to immunocastration and comprising the further step of using the results of the measurement as an indication of the likelihood of the success of the immunocastration.

4. The method of claim 2 wherein the animal is one which has been previously subjected to immunocastration and comprising the further step of using the results of the measurement as an indication of the likelihood of the success of the immunocastration.

5. The method of claim 1 wherein the sexual organ to be measured is part of the carcass of a slaughtered animal and further comprising the steps of locating by visual sensing means the sexual organ and positioning an ultrasonic transducer of an ultrasonic scanner in relation to the sexual organ to carry out the ultrasonic scanning.

6. The method of claim 5 wherein the step of locating the sexual organ by visual sensing means is further broken down into the steps of recording images of the subject animal, and calculating from the recorded images locators indicating the location of specific recognizable landmarks such as a leg of the animal being analysed, wherein the step of positioning the ultrasonic transducer is dependent upon these locators for orienting and guiding the ultrasonic transducer to the scrotal area.

7. The method of claim 6 further comprising the steps of comparing the range of measurements produced by the ultrasonic scanner when the ultrasonic transducer is positioned with preset values, generating a decision as to the most likely physiological function of the particular anatomical structure to which the ultrasonic transducer is pointing at that time, and determining if further guiding is required based on this decision.

8. Apparatus for determining the gonadal function of animal carcasses comprising means for conveying the carcasses, artificial vision means for locating a sexual organ of each of the carcasses as they are conveyed, an ultrasonic scanner having an ultrasonic transducer, means dependent on the artificial vision means for positioning the ultrasonic transducer in relation to the sexual organs to carry out ultrasonic scanning of the sexual organs, computing means connected to the ultrasonic scanner to compute from signals input from the ultrasonic scanner values for the volume or texture of the sexual organs and derive therefrom an indication of the gonadal function of the carcasses.

9. Apparatus according to claim 8 in which the artificial vision means comprises an image recording means together with software and a guiding means, the software being able to calculate from recorded images locators indicating the location of specific recognizable landmarks such as a leg of the animal being analysed, the guiding means being dependent upon these locators for orienting and guiding the ultrasonic transducer to the scrotal area.

10. The apparatus of claim 9 wherein the artificial vision means further comprises means for comparing the range of measurements produced by the ultrasonic scanner in its positioned state with preset values and generating a decision as to the most likely physiological function of the particular anatomical structure to which the scanner is pointing at that time, and based on this decision determining if further guiding is required.

11. The method of claim 2 wherein the sexual organ to be measured is part of the carcass of a slaughtered animal and further comprising the steps of locating by visual sensing means the sexual organ and positioning an ultrasonic transducer of an ultrasonic scanner in relation to the sexual organ to carry out the ultrasonic scanning.

12. The method of claim 3 wherein the sexual organ to be measured is part of the carcass of a slaughtered animal and further comprising the steps of locating by visual sensing means the sexual organ and positioning an ultrasonic transducer of an ultrasonic scanner in relation to the sexual organ to carry out the ultrasonic scanning.

\* \* \* \* \*